(12) United States Patent
Rimbaugh et al.

(10) Patent No.: US 8,986,336 B2
(45) Date of Patent: ***Mar. 24, 2015

(54) APPARATUS AND METHOD FOR DEPLOYMENT OF A BRONCHIAL OBSTRUCTION DEVICE

(75) Inventors: Jenni Rimbaugh, Bothell, WA (US); Lauri J. DeVore, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 521 days.

This patent is subject to a terminal disclaimer.

(21) Appl. No.: 13/013,070

(22) Filed: Jan. 25, 2011

(65) Prior Publication Data

US 2011/0203581 A1 Aug. 25, 2011

Related U.S. Application Data (63) Continuation of application No. 11/733,710, filed on Apr. 10, 2007, now Pat. No. 7,896,887, which is a continuation of application No. 10/418,929, filed on Apr. 17, 2003, now abandoned, which is a continuation of application No. 10/052,875, filed on Oct. 25, 2001, now Pat. No. 6,592,594.

(51) Int. Cl.
*A61F 11/00* (2006.01)
*A61M 29/00* (2006.01)
(Continued)

(52) U.S. Cl.
CPC ..... *A61B 17/12172* (2013.01); *A61B 17/12022* (2013.01); *A61B 17/12104* (2013.01);
(Continued)

(58) Field of Classification Search
CPC .................. A61B 17/12104; A61B 17/12172; A61B 2017/242; A61F 2002/043
USPC ......... 606/108, 191–198, 200, 213; 623/1.11, 623/1.12; 604/11, 15–18; 128/200.14–200.16, 207.14–207.16
See application file for complete search history.

(56) References Cited

U.S. PATENT DOCUMENTS

| | | | |
|---|---|---|---|
| 2,115,298 | A | 4/1938 | Brown |
| 2,728,225 | A | 12/1955 | Skibitzke |

(Continued)

FOREIGN PATENT DOCUMENTS

| | | |
|---|---|---|
| AU | 2002239759 | 5/2002 |
| AU | 2004263132 | 10/2010 |

(Continued)

OTHER PUBLICATIONS

Dillard et al., "Evaluation of a Novel Intra-bronchial Valve Device to Produce Lung Volume Reduction," Poster shown at conference in Jun. 2002.

(Continued)

*Primary Examiner* — Darwin Erezo
*Assistant Examiner* — Lindsey Bachman
(74) *Attorney, Agent, or Firm* — Knobbe Martens Olson & Bear LLP (57) ABSTRACT

An apparatus and method deploy a self-expandable bronchial obstruction device in an air passageway. The apparatus includes a catheter configured to be passed down the trachea. The apparatus further includes a capsule for housing the self-expandable bronchial obstruction device in a sterile environment. The capsule is configured to be advanced down the catheter. The capsule further includes a tubular extension. The capsule has a breakable seam so as to release the bronchial obstruction device in the air passageway upon a proximal force being exerted upon the bronchial obstruction device. The method includes guiding a conduit down a trachea into the air passageway. The method further includes advancing a capsule having a bronchial device therein down an internal lumen of the conduit into the air passageway. The method further includes releasing the bronchial device from the capsule. The method further includes deploying the bronchial device into the air passageway.

19 Claims, 3 Drawing Sheets

(51) Int. Cl.
*A61B 17/12* (2006.01)
*A61B 17/24* (2006.01)
*A61B 19/00* (2006.01)

(52) U.S. Cl.
CPC .......... *A61B17/24* (2013.01); *A61B 2017/1205* (2013.01); *A61B 2017/242* (2013.01); *A61B 2019/307* (2013.01)
USPC .......................................... 606/191; 606/108

(56) References Cited

U.S. PATENT DOCUMENTS

| | | |
|---|---|---|
| 2,832,078 A | 4/1958 | Williams |
| 2,981,254 A | 4/1961 | Vanderbilt |
| 3,320,972 A | 5/1967 | High et al. |
| 3,370,305 A | 2/1968 | Goott et al. |
| 3,445,916 A | 5/1969 | Schulte |
| 3,472,230 A | 10/1969 | Forgarty |
| 3,540,431 A | 11/1970 | Modin-Uddin |
| 3,617,060 A | 11/1971 | Iezzi |
| 3,657,744 A | 4/1972 | Ersek |
| 3,671,979 A | 6/1972 | Moulopoulos |
| 3,683,913 A | 8/1972 | Kurtz et al. |
| 3,757,783 A | 9/1973 | Alley |
| 3,760,808 A | 9/1973 | Bleuer |
| 3,788,327 A | 1/1974 | Donowitz et al. |
| 3,874,388 A | 4/1975 | King et al. |
| 3,889,657 A | 6/1975 | Baumgarten |
| 3,962,917 A | 6/1976 | Terada |
| 4,014,318 A | 3/1977 | Dockum et al. |
| 4,040,428 A | 8/1977 | Clifford |
| 4,056,854 A | 11/1977 | Boretos et al. |
| 4,084,268 A | 4/1978 | Ionescu et al. |
| 4,086,665 A | 5/1978 | Poirier |
| 4,205,282 A | 5/1980 | Gipprich |
| 4,212,463 A | 7/1980 | Repinski et al. |
| 4,218,782 A | 8/1980 | Rygg |
| 4,222,126 A | 9/1980 | Boretos et al. |
| 4,250,873 A | 2/1981 | Bonnet |
| 4,267,839 A | 5/1981 | Laufe et al. |
| 4,301,810 A | 11/1981 | Belman |
| 4,302,854 A | 12/1981 | Runge |
| 4,339,831 A | 7/1982 | Johnson |
| RE31,040 E | 9/1982 | Possis |
| 4,393,879 A | 7/1983 | Milgrom |
| 4,402,445 A | 9/1983 | Green |
| 4,403,616 A | 9/1983 | King |
| 4,456,016 A | 6/1984 | Nowacki et al. |
| 4,483,200 A | 11/1984 | Togawa et al. |
| 4,512,338 A | 4/1985 | Balko et al. |
| 4,533,137 A | 8/1985 | Sonne |
| 4,569,674 A | 2/1986 | Phillips et al. |
| 4,582,058 A | 4/1986 | Depel et al. |
| 4,583,541 A | 4/1986 | Barry |
| 4,592,741 A | 6/1986 | Vincent |
| 4,601,465 A | 7/1986 | Roy |
| 4,610,256 A | 9/1986 | Wallace |
| 4,619,246 A | 10/1986 | Molgaard-Nielsen et al. |
| 4,654,027 A | 3/1987 | Dragan et al. |
| 4,654,029 A | 3/1987 | D'Antonio |
| 4,681,110 A | 7/1987 | Wiktor |
| 4,684,363 A | 8/1987 | Ari et al. |
| 4,685,908 A | 8/1987 | Kurtz |
| 4,710,192 A | 12/1987 | Liotta et al. |
| 4,727,873 A | 3/1988 | Mobin-Uddin |
| 4,732,152 A | 3/1988 | Wallsten et al. |
| 4,745,925 A | 5/1988 | Dietz |
| 4,759,758 A | 7/1988 | Gabbay |
| 4,795,449 A | 1/1989 | Schneider et al. |
| 4,799,311 A | 1/1989 | Matsutani |
| 4,808,183 A | 2/1989 | Panje |
| 4,819,664 A | 4/1989 | Nazari |
| 4,822,354 A | 4/1989 | Elosegui |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,552 A | 8/1989 | Chaux |
| 4,852,568 A | 8/1989 | Kensey |
| 4,870,975 A | 10/1989 | Cronk et al. |
| 4,877,025 A | 10/1989 | Hanson |
| 4,881,939 A | 11/1989 | Newman |
| 4,888,015 A | 12/1989 | Domino |
| 4,896,668 A | 1/1990 | Popoff et al. |
| 4,908,028 A | 3/1990 | Colon et al. |
| 4,920,978 A | 5/1990 | Colvin |
| 4,934,999 A | 6/1990 | Bader |
| 4,936,823 A | 6/1990 | Colvin et al. |
| 4,968,294 A | 11/1990 | Salama |
| 4,973,047 A | 11/1990 | Norell |
| 4,979,505 A | 12/1990 | Cox |
| 4,984,581 A | 1/1991 | Stice |
| 4,995,872 A | 2/1991 | Ferrara |
| 5,002,772 A | 3/1991 | Curatolo et al. |
| 5,019,086 A | 5/1991 | Neward |
| 5,033,312 A | 7/1991 | Stupecky |
| 5,038,621 A | 8/1991 | Stupecky |
| 5,059,208 A | 10/1991 | Coe et al. |
| 5,061,274 A | 10/1991 | Kensey |
| 5,078,739 A | 1/1992 | Martin |
| 5,092,781 A | 3/1992 | Casciotti et al. |
| 5,111,823 A | 5/1992 | Cohen |
| 5,116,360 A | 5/1992 | Pinchuk et al. |
| 5,116,564 A | 5/1992 | Jansen et al. |
| 5,123,919 A | 6/1992 | Sauter et al. |
| 5,127,412 A | 7/1992 | Cohen |
| 5,135,488 A | 8/1992 | Foote et al. |
| 5,135,531 A | 8/1992 | Shiber |
| 5,147,369 A | 9/1992 | Wagner |
| 5,151,105 A | 9/1992 | Kwan-Gett |
| 5,158,548 A | 10/1992 | Lau et al. |
| 5,161,524 A | 11/1992 | Evans |
| 5,171,299 A | 12/1992 | Heitzmann et al. |
| 5,186,711 A | 2/1993 | Epstein |
| 5,197,485 A | 3/1993 | Grooters |
| 5,197,963 A | 3/1993 | Parins |
| 5,197,980 A | 3/1993 | Gorshkov et al. |
| 5,207,702 A | 5/1993 | Pearl |
| 5,226,429 A | 7/1993 | Kuzmak |
| 5,255,687 A | 10/1993 | McKenna |
| 5,275,169 A | 1/1994 | Afromowitz et al. |
| 5,281,229 A | 1/1994 | Neward |
| 5,283,063 A | 2/1994 | Freeman |
| 5,300,050 A | 4/1994 | Everett, Jr. et al. |
| 5,304,199 A | 4/1994 | Myers |
| 5,306,234 A | 4/1994 | Johnson |
| 5,314,473 A | 5/1994 | Godin |
| 5,339,805 A | 8/1994 | Parker |
| 5,342,298 A | 8/1994 | Michaels |
| 5,350,388 A | 9/1994 | Epstein |
| 5,352,240 A | 10/1994 | Ross |
| 5,353,470 A | 10/1994 | Bartlett |
| 5,356,412 A | 10/1994 | Golds et al. |
| 5,358,518 A | 10/1994 | Camilli |
| 5,366,475 A | 11/1994 | Voss et al. |
| 5,366,478 A | 11/1994 | Brinkerhoff et al. |
| 5,370,657 A | 12/1994 | Irie |
| 5,382,261 A | 1/1995 | Palmaz |
| 5,383,470 A | 1/1995 | Kolbly |
| 5,391,205 A | 2/1995 | Knight |
| 5,392,775 A | 2/1995 | Adkins, Jr. et al. |
| 5,398,844 A | 3/1995 | Zaslavsky |
| 5,409,019 A | 4/1995 | Wilk |
| 5,409,444 A | 4/1995 | Kensey et al. |
| 5,411,507 A | 5/1995 | Heckele |
| 5,411,552 A | 5/1995 | Andersen et al. |
| 5,413,599 A | 5/1995 | Imachi et al. |
| 5,415,658 A | 5/1995 | Kipela et al. |
| 5,415,660 A | 5/1995 | Campbell et al. |
| 5,417,226 A | 5/1995 | Juma |
| 5,421,325 A | 6/1995 | Cinberg et al. |
| 5,423,830 A | 6/1995 | Schneebaum et al. |
| 5,445,626 A | 8/1995 | Gigante |
| 5,453,090 A | 9/1995 | Martinez et al. |

(56) References Cited

U.S. PATENT DOCUMENTS

| | | | |
|---|---|---|---|
| 5,456,689 | A | 10/1995 | Kresch et al. |
| 5,459,544 | A | 10/1995 | Emura |
| 5,484,444 | A | 1/1996 | Braunschweiler et al. |
| 5,486,154 | A | 1/1996 | Kelleher |
| 5,490,860 | A | 2/1996 | Middle et al. |
| 5,499,995 | A | 3/1996 | Teirstein |
| 5,500,014 | A | 3/1996 | Quijano et al. |
| RE35,225 | E | 4/1996 | Herweck et al. |
| 5,503,638 | A | 4/1996 | Cooper |
| 5,507,754 | A | 4/1996 | Green et al. |
| 5,507,797 | A | 4/1996 | Suzuki |
| 5,509,900 | A | 4/1996 | Kirkman |
| 5,514,153 | A | 5/1996 | Bonutti et al. |
| 5,549,626 | A | 8/1996 | Miller et al. |
| 5,549,628 | A | 8/1996 | Cooper et al. |
| 5,562,608 | A | 10/1996 | Sekins et al. |
| 5,562,641 | A | 10/1996 | Flomenblit et al. |
| 5,562,728 | A | 10/1996 | Lazarus et al. |
| 5,575,293 | A | 11/1996 | Miller et al. |
| 5,593,413 | A | 1/1997 | Alexander |
| 5,603,698 | A | 2/1997 | Roberts et al. |
| 5,607,469 | A | 3/1997 | Frey |
| 5,645,565 | A | 7/1997 | Rudd et al. |
| 5,647,857 | A | 7/1997 | Anderson et al. |
| 5,649,953 | A | 7/1997 | Lefebvre |
| 5,660,175 | A | 8/1997 | Dayal |
| 5,662,622 | A | 9/1997 | Gore et al. |
| 5,662,713 | A | 9/1997 | Andersen et al. |
| 5,669,933 | A | 9/1997 | Simon et al. |
| 5,676,671 | A | 10/1997 | Inoue |
| 5,683,451 | A | 11/1997 | Lenker et al. |
| 5,690,644 | A | 11/1997 | Yurek et al. |
| 5,693,089 | A | 12/1997 | Inoue |
| 5,697,968 | A | 12/1997 | Rogers et al. |
| 5,702,343 | A | 12/1997 | Alferness |
| 5,702,409 | A | 12/1997 | Rayburn et al. |
| 5,725,519 | A | 3/1998 | Penner et al. |
| 5,741,271 | A | 4/1998 | Nakao et al. |
| 5,752,522 | A | 5/1998 | Murphy |
| 5,752,965 | A | 5/1998 | Francis et al. |
| 5,755,770 | A | 5/1998 | Ravenscroft |
| 5,763,979 | A | 6/1998 | Mukherjee et al. |
| 5,766,134 | A | 6/1998 | Lisak et al. |
| 5,769,892 | A | 6/1998 | Kingwell |
| 5,772,583 | A | 6/1998 | Wright et al. |
| 5,779,649 | A | 7/1998 | Herbert |
| 5,782,896 | A | 7/1998 | Chen et al. |
| 5,797,907 | A | 8/1998 | Clement |
| 5,797,920 | A | 8/1998 | Kim |
| 5,797,960 | A | 8/1998 | Stevens et al. |
| 5,800,339 | A | 9/1998 | Salama |
| 5,803,078 | A | 9/1998 | Brauner |
| 5,810,806 | A | 9/1998 | Ritchart et al. |
| 5,810,809 | A | 9/1998 | Rydell |
| 5,810,837 | A | 9/1998 | Hofmann et al. |
| 5,810,855 | A | 9/1998 | Rayburn et al. |
| 5,817,101 | A | 10/1998 | Fiedler |
| 2,479,805 | A | 11/1998 | Sabaratnam |
| 5,830,217 | A | 11/1998 | Ryan |
| 5,833,694 | A | 11/1998 | Poncet |
| 5,840,081 | A | 11/1998 | Andersen et al. |
| 5,851,232 | A | 12/1998 | Lois |
| 5,855,587 | A | 1/1999 | Hyon et al. |
| 5,855,597 | A | 1/1999 | Jayaraman |
| 5,855,601 | A | 1/1999 | Bessler et al. |
| 5,865,724 | A | 2/1999 | Palmer et al. |
| 5,876,434 | A | 3/1999 | Flomenblit et al. |
| 5,876,445 | A | 3/1999 | Andersen et al. |
| 5,895,387 | A | 4/1999 | Guerrero et al. |
| 5,902,312 | A | 5/1999 | Frater et al. |
| 5,911,756 | A | 6/1999 | Debry |
| 5,925,063 | A | 7/1999 | Khosravi |
| 5,944,738 | A | 8/1999 | Amplatz et al. |
| 5,947,997 | A | 9/1999 | Pavcnik et al. |
| 5,954,636 | A | 9/1999 | Schwartz et al. |
| 5,954,766 | A | 9/1999 | Zadno-Azizi et al. |
| 5,957,949 | A | 9/1999 | Leonhardt et al. |
| 5,957,978 | A | 9/1999 | Blom |
| 5,972,009 | A | 10/1999 | Fortier et al. |
| 5,976,158 | A | 11/1999 | Adams et al. |
| 5,976,174 | A | 11/1999 | Ruiz |
| 5,980,545 | A | 11/1999 | Pacala et al. |
| 5,984,965 | A | 11/1999 | Knapp et al. |
| 5,989,234 | A | 11/1999 | Valerio et al. |
| 6,003,517 | A | 12/1999 | Sheffield et al. |
| 6,007,575 | A | 12/1999 | Samuels |
| 6,009,614 | A | 1/2000 | Morales |
| 6,010,511 | A | 1/2000 | Murphy |
| 6,010,525 | A | 1/2000 | Bonutti et al. |
| 6,020,380 | A | 2/2000 | Killian |
| 6,024,759 | A | 2/2000 | Nuss et al. |
| 6,027,525 | A | 2/2000 | Suh et al. |
| 6,045,560 | A | 4/2000 | McKean et al. |
| 6,051,022 | A | 4/2000 | Cai et al. |
| 6,053,877 | A | 4/2000 | Banik et al. |
| 6,062,575 | A | 5/2000 | Mickel et al. |
| 6,068,635 | A | 5/2000 | Gianotti |
| 6,068,638 | A | 5/2000 | Makower |
| 6,077,214 | A | 6/2000 | Schweich et al. |
| 6,077,291 | A | 6/2000 | Das |
| 6,079,413 | A | 6/2000 | Baran |
| 6,083,141 | A | 7/2000 | Hougen |
| 6,083,255 | A | 7/2000 | Laufer et al. |
| 6,086,543 | A | 7/2000 | Anderson et al. |
| 6,090,035 | A | 7/2000 | Campbell et al. |
| 6,090,041 | A | 7/2000 | Clark |
| 6,096,027 | A | 8/2000 | Layne |
| 6,099,551 | A | 8/2000 | Gabbay |
| 6,102,885 | A | 8/2000 | Bass |
| 6,102,926 | A | 8/2000 | Tartaglia et al. |
| 6,123,663 | A | 9/2000 | Rebuffat |
| 6,132,458 | A | 10/2000 | Staehle et al. |
| 6,135,729 | A | 10/2000 | Aber |
| 6,135,991 | A | 10/2000 | Muni et al. |
| 6,141,855 | A | 11/2000 | Morales |
| 6,142,957 | A | 11/2000 | Diamond et al. |
| 6,146,357 | A | 11/2000 | Addis |
| 6,146,384 | A | 11/2000 | Lee et al. |
| 6,146,388 | A | 11/2000 | McDonald |
| 6,149,664 | A | 11/2000 | Kurz |
| 6,162,245 | A | 12/2000 | Jayaraman |
| 6,165,179 | A | 12/2000 | Cathcart et al. |
| 6,168,614 | B1 | 1/2001 | Andersen et al. |
| 6,168,617 | B1 | 1/2001 | Blaeser et al. |
| 6,174,307 | B1 | 1/2001 | Daniel et al. |
| 6,174,323 | B1 | 1/2001 | Biggs |
| 6,183,520 | B1 | 2/2001 | Pintauro et al. |
| 6,193,748 | B1 | 2/2001 | Thompson et al. |
| 6,200,333 | B1 | 3/2001 | Laufer |
| 6,203,551 | B1 | 3/2001 | Wu |
| 6,206,918 | B1 | 3/2001 | Campbell et al. |
| 6,210,338 | B1 | 4/2001 | Afremov et al. |
| 6,213,957 | B1 | 4/2001 | Milliman et al. |
| 6,231,587 | B1 | 5/2001 | Makower |
| 6,231,589 | B1 | 5/2001 | Wessman et al. |
| 6,234,996 | B1 | 5/2001 | Bagaoisan et al. |
| 6,238,334 | B1 | 5/2001 | Easterbrook, III et al. |
| 6,240,615 | B1 | 6/2001 | Kimes et al. |
| 6,241,654 | B1 | 6/2001 | Alferness |
| 6,241,678 | B1 | 6/2001 | Afremov et al. |
| 6,241,758 | B1 | 6/2001 | Cox |
| 6,242,472 | B1 | 6/2001 | Sekins et al. |
| 6,245,102 | B1 | 6/2001 | Jayaraman |
| 6,258,100 | B1 | 7/2001 | Alferness et al. |
| 6,264,700 | B1 | 7/2001 | Kilcoyne et al. |
| 6,267,775 | B1 | 7/2001 | Clerc et al. |
| 6,277,083 | B1 | 8/2001 | Tseng |
| 6,270,527 | B1 | 8/2001 | Campbell et al. |
| 6,280,398 | B1 | 8/2001 | Ritchart et al. |
| 6,287,290 | B1 | 9/2001 | Perkins et al. |
| 6,287,334 | B1 | 9/2001 | Moll et al. |
| 6,293,951 | B1 | 9/2001 | Alferness et al. |
| 6,296,639 | B1 | 10/2001 | Truckai et al. |
| 6,299,604 | B1 | 10/2001 | Ragheb et al. |

(56) References Cited

U.S. PATENT DOCUMENTS

| | | | |
|---|---|---|---|
| 6,302,893 B1 | 10/2001 | Limon et al. |
| 6,312,407 B1 | 11/2001 | Zadno-Azizi et al. |
| 6,322,522 B1 | 11/2001 | Zimmon |
| 6,325,777 B1 | 12/2001 | Zadno-Azizi et al. |
| 6,325,778 B1 | 12/2001 | Zadno-Azizi et al. |
| 6,327,505 B1 | 12/2001 | Medhkour et al. |
| 6,327,772 B1 | 12/2001 | Zadno-Azizi et al. |
| 6,328,689 B1 | 12/2001 | Gonzalez et al. |
| 6,331,183 B1 | 12/2001 | Suon |
| 6,338,728 B1 | 1/2002 | Valerio et al. |
| 6,342,062 B1 | 1/2002 | Suon et al. |
| 6,350,278 B1 | 2/2002 | Lenker et al. |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,425,916 B1 | 7/2002 | Garrison et al. |
| 6,428,561 B1 | 8/2002 | Johansson-Ruden et al. |
| 6,439,233 B1 | 8/2002 | Geertsema |
| 6,440,164 B1 | 8/2002 | DiMatteo et al. |
| 6,447,530 B1 | 9/2002 | Ostrovsky et al. |
| 6,454,727 B1 | 9/2002 | Burbank et al. |
| 6,454,754 B1 | 9/2002 | Frank |
| 6,458,076 B1 | 10/2002 | Pruitt |
| 6,458,153 B1 | 10/2002 | Bailey et al. |
| 6,471,718 B1 | 10/2002 | Staehle et al. |
| 6,471,979 B2 | 10/2002 | New et al. |
| 6,485,407 B2 | 11/2002 | Alferness et al. |
| 6,485,436 B1 | 11/2002 | Truckai et al. |
| 6,488,673 B1 | 12/2002 | Laufer et al. |
| 6,491,706 B1 | 12/2002 | Alferness et al. |
| 6,493,589 B1 | 12/2002 | Medhkour et al. |
| 6,503,272 B2 | 1/2003 | Duerig et al. |
| 6,506,166 B1 | 1/2003 | Hendler et al. |
| 6,510,846 B1 | 1/2003 | O'Rourke |
| 6,514,290 B1 | 2/2003 | Loomas |
| 6,527,761 B1 | 3/2003 | Soltesz et al. |
| 6,540,782 B1 | 4/2003 | Snyders |
| 6,544,192 B2 | 4/2003 | Starr et al. |
| 6,544,291 B2 | 4/2003 | Taylor |
| 6,551,255 B2 | 4/2003 | Van Bladel et al. |
| 6,551,303 B1 | 4/2003 | Van Tassel et al. |
| 6,558,429 B2 | 5/2003 | Taylor |
| 6,568,387 B2 | 5/2003 | Davenport et al. |
| 6,569,166 B2 | 5/2003 | Gonzalez |
| 6,585,639 B1 | 7/2003 | Kotmel et al. |
| 6,589,240 B2 | 7/2003 | Hinchliffe |
| 6,589,256 B2 | 7/2003 | Forber |
| 6,592,594 B2 | 7/2003 | Rimbaugh et al. |
| 6,599,304 B1 * | 7/2003 | Selmon et al. ............ 606/159 |
| 6,599,311 B1 | 7/2003 | Biggs et al. |
| 6,600,307 B2 | 7/2003 | Turski |
| 6,610,043 B1 | 8/2003 | Ingenito |
| 6,620,095 B2 | 9/2003 | Taheri |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,363 B1 | 10/2003 | Danek et al. |
| 6,638,285 B2 | 10/2003 | Gabbay |
| 6,648,897 B2 | 11/2003 | Hamilton |
| 6,669,724 B2 | 12/2003 | Park et al. |
| 6,673,070 B2 | 1/2004 | Edwards et al. |
| 6,679,264 B1 | 1/2004 | Deem et al. |
| 6,682,250 B2 | 1/2004 | Banks |
| 6,682,520 B2 | 1/2004 | Ingenito |
| 6,694,979 B2 | 2/2004 | Deem et al. |
| 6,709,401 B2 | 3/2004 | Perkins |
| 6,712,812 B2 | 3/2004 | Roschak et al. |
| 6,716,208 B2 | 4/2004 | Humes |
| 6,743,259 B2 | 6/2004 | Ginn |
| 6,746,686 B2 | 6/2004 | Hughes et al. |
| 6,749,606 B2 | 6/2004 | Keast et al. |
| 6,840,952 B2 | 1/2005 | Saker et al. |
| 6,849,049 B2 | 2/2005 | Starr et al. |
| 6,849,084 B2 | 2/2005 | Rabkin et al. |
| 6,852,108 B2 | 2/2005 | Barry et al. |
| 6,860,847 B2 | 3/2005 | Alferness et al. |
| 6,886,558 B2 | 5/2005 | Tanaka |
| 6,887,256 B2 | 5/2005 | Gilson |
| 6,904,909 B2 | 6/2005 | Andreas et al. |
| 6,911,028 B2 | 6/2005 | Shadduck |
| 6,941,950 B2 | 9/2005 | Wilson et al. |
| 6,951,571 B1 | 10/2005 | Srivastava |
| 6,955,675 B2 | 10/2005 | Jain |
| 6,958,059 B2 | 10/2005 | Zadno-Azizi |
| 6,958,076 B2 | 10/2005 | Acosta et al. |
| 6,989,027 B2 | 1/2006 | Allen et al. |
| 6,997,951 B2 | 2/2006 | Solem et al. |
| 7,011,094 B2 | 3/2006 | Rapacki et al. |
| 7,077,851 B2 | 7/2006 | Lutze et al. |
| 7,086,398 B2 | 8/2006 | Tanaka |
| 7,100,616 B2 | 9/2006 | Springmeyer |
| 7,141,046 B2 | 11/2006 | Perkins et al. |
| 7,169,140 B1 | 1/2007 | Kume |
| 7,175,644 B2 | 2/2007 | Cooper et al. |
| 7,207,946 B2 | 4/2007 | Sirokman |
| 7,252,086 B2 | 8/2007 | Tanaka |
| 7,273,469 B1 | 9/2007 | Chan et al. |
| 7,278,430 B2 | 10/2007 | Kumar |
| 7,344,553 B2 | 3/2008 | Opolski et al. |
| 7,357,795 B2 | 4/2008 | Kaji et al. |
| 7,412,977 B2 | 8/2008 | Fields et al. |
| 7,422,584 B2 | 9/2008 | Loomas et al. |
| 7,434,578 B2 | 10/2008 | Dillard et al. |
| 7,476,203 B2 | 1/2009 | DeVore et al. |
| 7,530,995 B2 | 5/2009 | Quijano et al. |
| 7,637,934 B2 | 12/2009 | Mangiardi et al. |
| 7,704,268 B2 | 4/2010 | Chanduszko |
| 7,842,061 B2 | 11/2010 | Dillard et al. |
| 7,854,228 B2 | 12/2010 | Wilson et al. |
| 7,862,500 B2 | 1/2011 | Khairkhahan et al. |
| 7,875,048 B2 | 1/2011 | Dillard et al. |
| 7,913,698 B2 | 3/2011 | Barry et al. |
| 8,711,809 B2 | 5/2012 | Mavani et al. |
| 8,192,478 B2 | 6/2012 | Khairkhahan et al. |
| 2001/0001817 A1 | 5/2001 | Humes |
| 2001/0010017 A1 | 7/2001 | Letac et al. |
| 2001/0012949 A1 | 8/2001 | Forber |
| 2001/0025132 A1 | 9/2001 | Alferness et al. |
| 2001/0034518 A1 | 10/2001 | Edwards et al. |
| 2001/0037808 A1 | 11/2001 | Deem et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0002401 A1 | 1/2002 | McGuckin et al. |
| 2002/0007831 A1 | 1/2002 | Davenport et al. |
| 2002/0029004 A1 | 3/2002 | Starr et al. |
| 2002/0038125 A1 | 3/2002 | Hamilton |
| 2002/0052626 A1 | 5/2002 | Gilson |
| 2002/0062120 A1 | 5/2002 | Perkins et al. |
| 2002/0072730 A1 | 6/2002 | McGill et al. |
| 2002/0077564 A1 | 6/2002 | Campbell et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0091411 A1 | 7/2002 | Saker et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | Devore et al. |
| 2002/0123749 A1 | 9/2002 | Jain |
| 2002/0138135 A1 | 9/2002 | Duerig et al. |
| 2002/0147462 A1 | 10/2002 | Mair et al. |
| 2003/0013935 A1 | 1/2003 | Alferness et al. |
| 2003/0018327 A1 | 1/2003 | Truckai et al. |
| 2003/0018344 A1 | 1/2003 | Kaji et al. |
| 2003/0024527 A1 | 2/2003 | Ginn |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0070682 A1 | 4/2003 | Wilson et al. |
| 2003/0083671 A1 | 5/2003 | Rimbaugh et al. |
| 2003/0083730 A1 | 5/2003 | Stinson |

(56) References Cited

U.S. PATENT DOCUMENTS

| | | |
|---|---|---|
| 2003/0109869 A1 | 6/2003 | Shadduck |
| 2003/0125763 A1 | 7/2003 | McInnes |
| 2003/0127090 A1 | 7/2003 | Gifford et al. |
| 2003/0154988 A1 | 8/2003 | DeVore et al. |
| 2003/0158515 A1 | 8/2003 | Gonzalez et al. |
| 2003/0167065 A1 | 9/2003 | Kumar |
| 2003/0181890 A1 | 9/2003 | Schulze et al. |
| 2003/0181922 A1 | 9/2003 | Alferness |
| 2003/0199888 A1 | 10/2003 | Lutze et al. |
| 2003/0199972 A1 | 10/2003 | Zadno-Azizi et al. |
| 2003/0212337 A1 | 11/2003 | Sirokman |
| 2003/0225445 A1 | 12/2003 | Derus et al. |
| 2003/0228344 A1 | 12/2003 | Fields et al. |
| 2004/0024356 A1 | 2/2004 | Tanaka |
| 2004/0039250 A1 | 2/2004 | Tholfsen et al. |
| 2004/0039443 A1 | 2/2004 | Solem et al. |
| 2004/0040555 A1 | 3/2004 | Tanaka |
| 2004/0060563 A1 | 4/2004 | Rapacki et al. |
| 2004/0127912 A1 | 7/2004 | Rabkin et al. |
| 2004/0143282 A1 | 7/2004 | Dillard et al. |
| 2004/0143283 A1 | 7/2004 | McGill et al. |
| 2004/0167636 A1 | 8/2004 | Dillard et al. |
| 2004/0200484 A1 | 10/2004 | Springmeyer |
| 2004/0206349 A1 | 10/2004 | Alferness |
| 2004/0210248 A1 | 10/2004 | Gordon et al. |
| 2004/0210306 A1 | 10/2004 | Quijano et al. |
| 2004/0211434 A1 | 10/2004 | Loomas et al. |
| 2004/0244802 A1 | 12/2004 | Tanaka |
| 2005/0033344 A1 | 2/2005 | Dillard et al. |
| 2005/0080434 A1 | 4/2005 | Chung et al. |
| 2005/0096721 A1 | 5/2005 | Mangin et al. |
| 2005/0137611 A1 | 6/2005 | Escudero et al. |
| 2005/0137714 A1 | 6/2005 | Gonzalez et al. |
| 2005/0145253 A1 | 7/2005 | Wilson et al. |
| 2005/0166925 A1 | 8/2005 | Wilson et al. |
| 2005/0222580 A1 | 10/2005 | Gifford, III et al. |
| 2005/0245894 A1 | 11/2005 | Zadno-Azizi |
| 2005/0267323 A1 | 12/2005 | Dorros et al. |
| 2006/0064123 A1 | 3/2006 | Bonnette et al. |
| 2006/0100687 A1 | 5/2006 | Fahey et al. |
| 2006/0155217 A1 | 7/2006 | DeVore |
| 2006/0241745 A1 | 10/2006 | Solem et al. |
| 2006/0270940 A1 | 11/2006 | Tsukashima et al. |
| 2007/0185531 A1 | 8/2007 | Rimbaugh et al. |
| 2007/0209204 A1 | 9/2007 | Chase et al. |
| 2007/0221230 A1 | 9/2007 | Thompson et al. |
| 2007/0225747 A1 | 9/2007 | Perkins et al. |
| 2007/0232992 A1 | 10/2007 | Kutsko et al. |
| 2007/0250022 A1 | 10/2007 | Sirokman |
| 2008/0132989 A1 | 6/2008 | Snow et al. |
| 2008/0149446 A1 | 6/2008 | Schuurman |
| 2009/0182369 A1 | 7/2009 | Gonzalez |
| 2009/0188508 A1 | 7/2009 | Smith, Jr. |
| 2009/0205667 A1 | 8/2009 | Alferness et al. |
| 2009/0292262 A1 | 11/2009 | Adams et al. |
| 2010/0082089 A1 | 4/2010 | Quadri et al. |
| 2010/0262071 A1 | 10/2010 | Kutsko et al. |
| 2013/0190679 A1 | 7/2013 | Springmeyer |

FOREIGN PATENT DOCUMENTS

| | | |
|---|---|---|
| AU | 2007241066 | 9/2011 |
| CA | 2308186 | 5/1999 |
| CA | 2375752 | 1/2001 |
| CA | 2401331 | 3/2001 |
| CA | 2408923 | 11/2001 |
| CA | 2603948 | 4/2005 |
| CN | 101868199 | 10/2010 |
| CN | 102058443 | 5/2011 |
| CN | 200780019455.6 | 6/2012 |
| CN | 102579155 | 7/2012 |
| DE | 100 04 979 | 8/2000 |
| EP | 0 665 029 | 8/1995 |
| EP | 0 743 071 | 11/1996 |
| EP | 1 078 601 | 2/2001 |
| EP | 1 151 729 A1 | 11/2001 |
| EP | 1157663 A1 | 11/2001 |
| EP | 1 206 276 | 5/2002 |
| EP | 1 198 269 | 10/2009 |
| EP | 1 494 632 | 12/2010 |
| EP | 03 716 212 | 12/2010 |
| EP | 2 353 557 | 8/2011 |
| EP | 10 714 725.8 | 8/2011 |
| EP | 2 416 737 | 2/2012 |
| EP | 2 520 321 | 11/2012 |
| EP | 1 496 790 | 6/2013 |
| EP | 2 641 572 | 9/2013 |
| FR | 2 773 702 | 7/1999 |
| GB | 2 082 071 | 3/1982 |
| GB | 2 324 729 A | 11/1998 |
| GB | 2 348 138 | 9/2000 |
| HK | 1153639 | 4/2012 |
| JP | 58-163332 | 9/1983 |
| JP | H11-513577 | 11/1990 |
| JP | 60-10740 | 1/1994 |
| JP | H08-19544 | 1/1996 |
| JP | 2003-503162 | 1/2003 |
| JP | 2003-533266 | 11/2003 |
| JP | 2004-535887 | 12/2004 |
| JP | 2005-527297 | 9/2005 |
| JP | 3742010 | 11/2005 |
| JP | 4387803 B2 | 10/2009 |
| JP | 2011-500171 | 1/2011 |
| JP | 2011-523363 | 8/2011 |
| JP | 2013107784 | 5/2013 |
| JP | 2009-503031 | 7/2013 |
| RU | 2140211 | 10/1999 |
| RU | 2440066 | 1/2012 |
| SU | 852321 | 8/1981 |
| SU | 1371700 | 2/1988 |
| SU | 1593651 | 9/1990 |
| WO | WO 88/09683 | 12/1988 |
| WO | WO 90/03152 | 4/1990 |
| WO | WO 92/10725 | 6/1992 |
| WO | WO 94/26175 | 11/1994 |
| WO | WO 95/32018 | 11/1995 |
| WO | WO 96/04875 | 2/1996 |
| WO | WO 96/34582 | 11/1996 |
| WO | WO 96/37167 | 11/1996 |
| WO | WO 97/09932 | 3/1997 |
| WO | WO 97/13471 | 4/1997 |
| WO | WO 97/27893 | 8/1997 |
| WO | WO 97/42871 | 11/1997 |
| WO | WO 97/44085 | 11/1997 |
| WO | WO 98/00840 | 1/1998 |
| WO | WO 98/01084 | 1/1998 |
| WO | WO 98/08441 | 3/1998 |
| WO | WO 98/19633 | 5/1998 |
| WO | WO 98/39047 | 9/1998 |
| WO | WO 98/44854 | 10/1998 |
| WO | WO 98/48706 | 11/1998 |
| WO | WO 99/01076 | 1/1999 |
| WO | WO 99/13801 | 3/1999 |
| WO | WO 99/26692 | 6/1999 |
| WO | WO 99/32040 | 7/1999 |
| WO | WO 99/42059 | 8/1999 |
| WO | WO 99/42161 | 8/1999 |
| WO | WO 99/59503 | 11/1999 |
| WO | WO 99/64109 | 12/1999 |
| WO | WO 00/12011 | 3/2000 |
| WO | WO 00/18329 | 4/2000 |
| WO | WO 00/27292 A | 5/2000 |
| WO | WO 00/42950 | 7/2000 |
| WO | WO 00/51500 A | 9/2000 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | WO 01/02042 | 1/2001 |
| WO | WO 01/03641 | 1/2001 |
| WO | WO 01/03642 | 1/2001 |
| WO | WO 01/05334 | 1/2001 |
| WO | WO 01/10313 | 2/2001 |

(56) References Cited

FOREIGN PATENT DOCUMENTS

| | | |
|---|---|---|
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/15604 | 3/2001 |
| WO | WO 01/28433 | 4/2001 |
| WO | WO 01/30266 | 5/2001 |
| WO | WO 01/30268 | 5/2001 |
| WO | WO 01/37897 | 5/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | WO 01/66190 | 9/2001 |
| WO | WO 01/70114 | 9/2001 |
| WO | WO 01/74271 | 10/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | WO 02/22053 | 3/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/56794 | 7/2002 |
| WO | WO 02/064045 | 8/2002 |
| WO | WO 02/064190 | 8/2002 |
| WO | WO 02/069808 | 9/2002 |
| WO | WO 02/069823 | 9/2002 |
| WO | WO 02/087447 | 11/2002 |
| WO | WO 02/094087 | 11/2002 |
| WO | WO 03/022124 | 3/2003 |
| WO | WO 03/030975 | 4/2003 |
| WO | WO 03/003946 | 5/2003 |
| WO | WO 03/034927 | 5/2003 |
| WO | WO 03/041779 | 5/2003 |
| WO | WO 03/047468 | 6/2003 |
| WO | WO 03/078579 | 9/2003 |
| WO | WO 03/079944 | 10/2003 |
| WO | WO 03/088820 | 10/2003 |
| WO | WO 03/094996 | 11/2003 |
| WO | WO 03/099164 | 12/2003 |
| WO | WO 2004/010845 | 2/2004 |
| WO | WO 2004/080347 | 9/2004 |
| WO | WO 2005/013835 | 2/2005 |
| WO | WO 2006/034166 | 3/2006 |
| WO | WO 2006/124822 | 11/2006 |
| WO | WO 2007/123690 | 11/2007 |
| WO | WO 2009/049261 | 4/2009 |
| WO | WO 2009/135070 | 11/2009 |
| WO | WO 2010/118056 | 10/2010 |
| WO | WO 2012/158152 | 11/2012 |

OTHER PUBLICATIONS

EWS Endobronchial Watanabe Spigots, Novatech, edited Apr. 17, 2002.
Harris et al., "The Experimental Production in Dogs of Emphysema with Associated Asthmatic Syndrome by Means of an Intratracheal Ball Valve," J. Exp Med 30:1919; 75-88.
Horiuchi et al: Three Cases of Intractable Pneumothorax Treated Successfully by Bronchial Embolization using Silicon; JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.
Jones et al: Closure of a Benign Broncho-Oesophageal Fistula by Endoscopic Injection of Bovine Collagen, Cyanocrylate Glue and Gelfoam; 1996, pp. 53-55 Aust. N.Z. J. Surg.
Lewis et al., "Pulmonary Interstitial Emphysema: Selective Bronchial Occlusion with a Swan-Ganz Catheter." Archives of Disease in Childhood, 63:1988, 313-315.
Mathew et al. "Selective Bronchial Obstruction for Treatment of Bullous Interstitial Emphysema," J. of Ped. 96:1980, 475-477.
Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.
Puhakka et al., "Acute Bronchial Obstruction: An Experimental Rabbit Model Study." Int. J. Of Pediatric Otorhinolaryngology. 18:1989, 107-118.
Snider et al., "The Definition of Emphysema: Report of the National Heart Lung and Blood Institute, Division of Lung Diseases Workshop", Am. Rev. Respir. Dis., 132:182-185, 1985.
Watanabe et al: Bronchial Embolization Using Dental Impression Material in a Case of Pyelo-bronchial Fistula with Candida Fungemia; 1991. Journal of the Japan Society for Bronchology, pp. 607-610.
U.S. Appl. No. 13/388,621, filed Mar. 29, 2013, Alferness.
U.S. Appl. No. 13/787,052, filed Mar. 6, 2013, Alferness et al.
Amendment mailed Mar. 3, 2004 in response to Office Action dated Oct. 3, 2003 in the related copending U.S. Appl. No. 09/951,105.
Andre A. Kulisz, Autocath 100—Nonsurgical, Intraurethral Bladder Control Device for Urinary Incontinent and Urinary Retentive Women—Another Dr. Kulisz's Development, http://www.kulisz.com/autocath.htm, 2003, 3 pp.
April et al. "Correction of Funnel-Chest According to Senning-Johnson", Schweiz. Rundchau. Med. (PRAXIS) 79, Nr. 12 (1980) pp. 356-360.
Chest Drains, from webmaster@atroi.ed/cp., from website Mar. 21, 2002; pp. 1-3.
Chest Drains, from webmaster@surgical-tutor.org.uk; from Website on Mar. 21, 2002; pp. 1-3.
EDO Ceramics Products and Services, from webmaster@edocorp.com; from website on Mar. 21, 2002; pp. 1,2.
Ellis, James H., Balloon Catheter Occlusion of Bronchopleural Fistulae, May 7, 1981, AJR: 138, Jan. 1982, p. 157-159.
Exploring Chest Drain Options; from webmaster google.com; RNWeb: Continuing Education; from website on Mar. 21, 2002; pp. 1-6.
J&J Gateway LLC Web Page: Steps in the Mammotome Surgical Procedure; Surgical Technique, Dec. 28, 2001; p. 1-3.
Marco: Bubble Detector, from webmaster@marco.de, from Website on Mar. 21, 2002; pp. 1-3.
Oasis Dry Suction Chest Drains; Instructions for Use; Atrium Medical Corporation, Hudson New Hampshire, on Mar. 27, 2002,pp. 1-4.
Ochsner et al. "Chone-Chondrosternon", Journal of Thoracic Surgery, vol. 8, No. 5, Jun. 1939, pp. 469-511.
Shamberger, "Congenital Chest Wall Deformities" Current Problems in Surgery vol. XXXIII, No. 6, Jun. 1996, pp. 470-543.
SIII Control and Display Modules; from webmaster@stoeckert.de; from website on Mar. 21, 2002, pp. 15.
Tanase, D., et al.: "Investigation of Multi-Sensor Techniques for Cardiac-Output Measurements in Intensive Care," Microtechnology in Medicine and Biology, 2005, 3rd IEEE/EMB, Special Topic Conference, pp. 122-125.
Tube Thoracostomy; from webmaster@merck.com/pubs/manual; from Website Mar. 21, 2003, pp. 1,2.
Understanding Chest Drainage; from webmaster@nursingceu.com; from website on Mar. 21, 2002; pp. 1-15.

* cited by examiner

APPARATUS AND METHOD FOR DEPLOYMENT OF A BRONCHIAL OBSTRUCTION DEVICE

CROSS-REFERENCE TO RELATED APPLICATIONS

This application is a continuation of U.S. patent application Ser. No. 11/733,710, filed Apr. 10, 2007, now U.S. Pat. No. 7,896,887 titled APPARATUS AND METHOD FOR DEPLOYMENT OF A BRONCHIAL OBSTRUCTION DEVICE, which is a continuation of U.S. patent application Ser. No. 10/418,929, filed Apr. 17, 2003, titled BRONCHIAL OBSTRUCTION DEVICE DEPLOYMENT SYSTEM AND METHOD, which is a continuation of U.S. patent application Ser. No. 10/052,875, filed on Oct. 25, 2001, now U.S. Pat. No. 6,592,594, titled BRONCHIAL OBSTRUCTION DEVICE DEPLOYMENT SYSTEM AND METHOD. The entire disclosure of each of the above-noted prior applications is hereby incorporated by reference herein and made a part of this specification.

BACKGROUND OF THE INVENTION

1. Field of the Invention

The present invention is generally directed to a treatment of Chronic Obstructive Pulmonary Disease (COPD). The present invention is more particularly directed to an apparatus and method for deploying a bronchial device.

2. Description of the Related Art

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and has increased 33% since 1979.

COPD affects the patient's whole life. It has three main symptoms: cough; breathlessness; and wheeze. At first, breathlessness may be noticed when running for a bus, digging in the garden, or walking up a hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosteroids, may be required. Lastly, antibiotics may be required to prevent infections, and influenza and pneumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopping reimbursing for LVRS. Unfortunately, data is relatively scarce and many factors conspire to make what data exists difficult to interpret. The procedure is currently under review in a controlled clinical trial. What data does exist tends to indicate that patients benefited from the procedure in terms of an increase in forced expiratory volume, a decrease in total lung capacity, and a significant improvement in lung function, dyspnea, and quality of life. However, the surgery is not without potential complications. Lung tissue is very thin and fragile. Hence, it is difficult to suture after sectioning. This gives rise to potential infection and air leaks. In fact, nearly thirty percent (30%) of such surgeries result in air leaks.

Improvements in pulmonary functions after LVRS have been attributed to at least four possible mechanisms. These include enhanced elastic recoil, correction of ventilation/perfusion mismatch, improved efficiency of respiratory musculature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all parties.

In view of the need in the art for new and improved therapies for COPD which provide more permanent results than pharmacotherapy while being less invasive and traumatic than LVRS, at least two new therapies have recently been proposed. Both of these new therapies provide lung size reduction by permanently or temporarily collapsing at least a portion of a lung.

In accordance with a first one of these therapies, and as described in U.S. Pat. No. 6,258,100 assigned to the assignee of the present invention and incorporated herein by reference, a lung may be collapsed by obstructing an air passageway communicating with the lung portion to be collapsed. The air passageway may be obstructed by placing a bronchial obstruction device in the air passageway. The bronchial obstruction device may be a plug-like device which precludes air flow in both directions or a one-way valve which permits air to be exhaled from the lung portion to be collapsed while precluding air from being inhaled into the lung portion. Once the air passageway is sealed, the residual air within the lung will be absorbed over time to cause the lung portion to collapse.

As further described in U.S. Pat. No. 6,258,100, the lung portion may be collapsed by inserting a conduit into the air passageway communicating with the lung portion to be collapsed. An obstruction device, such as a one-way valve is then advanced down the conduit into the air passageway. The obstruction device is then deployed in the air passageway for sealing the air passageway and causing the lung portion to be collapsed.

The second therapy is fully described in copending U.S. patent application Ser. No. 09/534,244, filed Mar. 23, 2000, for LUNG CONSTRICTION APPARATUS AND METHOD and is also assigned to the assignee of the present invention. As described therein, a lung constriction device including a sleeve of elastic material is configured to cover at least a portion of a lung. The sleeve has a pair of opened ends to permit the lung portion to be drawn into the sleeve. Once drawn therein, the lung portion is constricted by the sleeve to reduce the size of the lung portion.

Both therapies hold great promise for treating COPD. Neither therapy requires sectioning and suturing of lung tissue.

While either therapy alone would be effective in providing lung size reduction and treatment of COPD, it has recently been proposed that the therapies may be combined for more effective treatment. More specifically, it has been proposed that the therapies could be administered in series, with the first mentioned therapy first applied acutely for evaluation of the effectiveness of lung size reduction in a patient and which lung portions should be reduced in size to obtain the best results. The first therapy is ideal for this as it is noninvasive and could be administered in a physician's office. Once the effectiveness of lung size reduction is confirmed and the identity of the lung portions to be collapsed is determined, the more invasive second mentioned therapy may be administered.

In order to employ the first-mentioned therapy described in U.S. Pat. No. 6,258,100, it is necessary to deploy the bronchial obstruction device within an air passageway. The deployment must be reliable in that the bronchial device must be deployed in a well-controlled manner to assure placement in the proper location. The bronchial device must also be deployed in a sterile manner. Patients suffering from COPD generally have compromised health. Sterile deployment may therefore prevent a catastrophic infection from occurring in those patients who are in a weakened state. The present invention addresses these issues by providing bronchial obstruction device deployment systems and methods which provide more reliable device placement and sterile deployment conditions.

SUMMARY OF THE INVENTION

The present invention provides a device for deploying a self-expandable bronchial obstruction device in an air passageway. The device includes a catheter configured to be passed down the trachea. The device further includes a capsule for housing the self-expandable bronchial obstruction device in a sterile environment. The capsule is further configured to be advanced down the catheter. The capsule further includes a tubular extension. The capsule has a breakable seam so as to release the bronchial device in the air passageway upon a proximal force being exerted upon the bronchial obstruction device. Additionally, the capsule may be formed of flexible material for collapsing within the catheter.

The invention still further provides a method of deploying a bronchial device in an air passageway. The method includes guiding a conduit down a trachea into the air passageway. The method further includes advancing a capsule having a bronchial device therein down an internal lumen of the conduit into the air passageway. The method further includes releasing the bronchial device from the capsule. The method further includes deploying the bronchial device into the air passageway. Additionally, the capsule may comprise a breakable seam from which the bronchial device can be released. The method may further comprise pushing the bronchial device from the capsule.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

DETAILED DESCRIPTION OF THE PREFERRED EMBODIMENT

Figure 1:
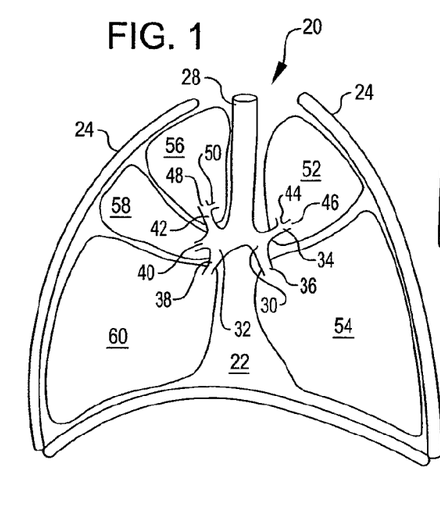
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
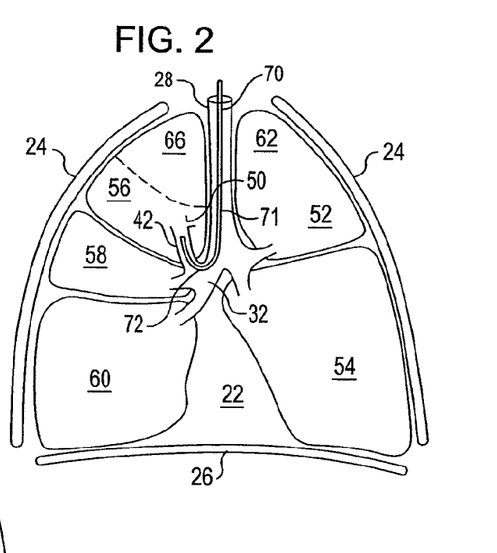
FIG. 2 is a sectional view similar to FIG. 1, but illustrating a respiratory system suffering from COPD and the execution of a first step in treating the COPD condition in accordance with the present invention.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving the diaphragm 28. Instead, in order to create the negative pressure in the thorax 22 required for breathing, this individual must move the chest wall outwardly to increase the volume of the thorax. This results in inefficient breathing causing these individuals to breathe rapidly with shallow breaths. It has been found that the apex portion 62 and 66 of the upper lung lobes 52 and 56, respectively, are most affected by COPD.

In accordance with the present invention, COPD treatment or evaluation is initiated by feeding a conduit 70 down the trachea 28, into a mainstream bronchus such as the right mainstem bronchus 32, and into an air passageway such as the bronchial branch 42 or the bronchial sub-branch 50. The conduit 70 may be a catheter or a bronchoscope as are well-known in the art. A bronchial obstruction device, contained within a housing, is then advanced down an internal lumen 71 of the conduit 70 and then released from the housing in the air passageway. Once deployed, the obstruction device precludes inhaled air from entering the lung portion to be collapsed. It is preferable that the obstruction device take the form of a one-way valve. In addition to precluding inhaled air from entering the lung portion, the device further allows air within the lung portion to be exhaled. This results in more rapid collapse of the lung portion. However, obstruction devices which preclude both inhaled and exhaled air flow may be deployed by the apparatus and method of the invention.

Figure 3:
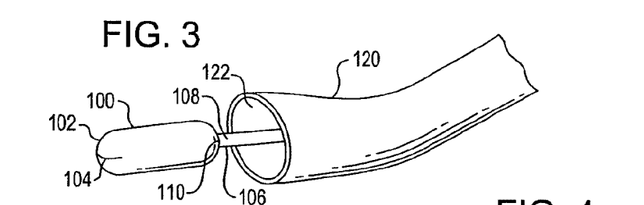
FIG. 3 is a perspective view, illustrating a housing for the bronchial obstruction device and a conduit embodying the present invention.
Figures 4, 5:
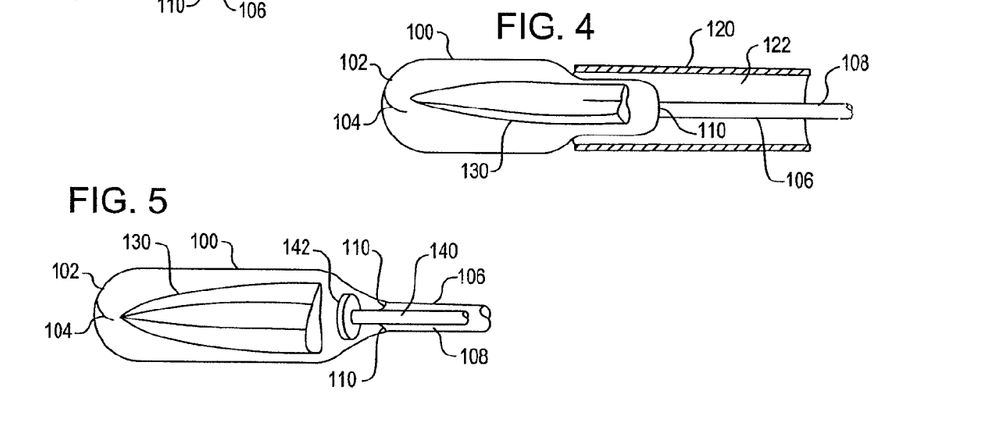
FIG. 4 is a partial cross-sectional view of the housing exiting the distal end of the conduit.
FIG. 5 is a side view illustrating a pusher just prior to engaging the bronchial obstruction device.

FIGS. 3 and 4 show a bronchial obstruction device housing 100 and a conduit 120 embodying the present invention. The housing 100 forms a sealed capsule structure for housing a bronchial obstruction device 130 to be deployed within an air passageway. The housing 100 has a rounded distal end 102. The rounded configuration of the distal end 102 assists in the guiding of the housing to a desired location within the air passageway. The housing 100, as best seen in FIG. 4 is formed of a flexible, biocompatible material for collapsing within the internal lumen 122 of the conduit 120 as it is advanced through the conduit.

The housing distal end 102 further includes a score or notch 104 to enable the distal end 104 of the housing 100 to be broken-away during deployment of the device 130 without breaking the seal within the housing 100 until the time of deployment.

The housing still further includes a tubular extension 106 having an internal lumen 108. The lumen 108 communicates with the interior of the housing 100 during deployment of the device 130 but may be separated therefrom by a breakable wall 110. As will be seen subsequently, the breakable wall 110 maintains the seal of the housing while permitting a pusher to be advanced through the lumen 108 to break through the wall 110 at the time of deployment to then engage the device 130. With the device 130 thus engaged, further distal advancement of the pusher causes the device to break through the distal end 102 of the housing weakened by the notch 104. Still further advancement of the pusher then releases the device 130 from the housing 100 for deployment of the device 130 at the desired location within the air passageway.

Hence, the device 130 may be deployed in a controlled manner. Further, the seal of the housing 100 is not broken until the time of deployment, rendering the process sterile.

Figure 6:
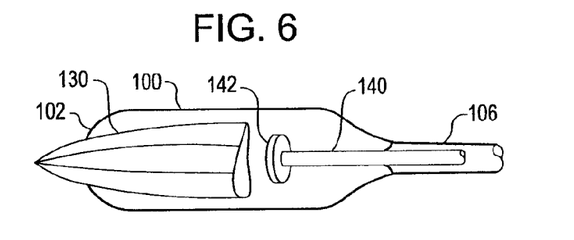
FIG. 6 is another side view illustrating the device being released from the housing by the pusher.
Figure 7:
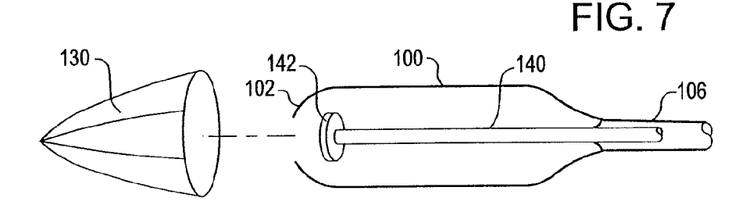
FIG. 7 is another side view of the device, the housing, and the pusher immediately after the device is released from the housing.

FIGS. 5-7 better illustrate the foregoing process. In FIG. 5 it may be seen that the pusher 140 has been advanced through the lumen 108 of the extension 106 and has broken through the wall 110 previously separating the housing 100 from the lumen 108. In accordance with this embodiment, the pusher includes a disc-shaped end 142 for engaging the device 130. Alternatively, the pusher 140 may be an appropriately shaped wire or rod. The end 142 may have a diameter dimension slightly less than the diameter dimension of the lumen 108. Alternatively, the extension 106 may be formed of material flexible enough to permit the end 142 to be slightly greater than the diameter of the lumen 108. This allows the extension 106 to be slightly deformed as the end 142 of the pusher 140 is advanced down the extension. In either arrangement, the pusher is slidable down the extension to break through the wall 110 and enter the housing 100.

As seen in FIG. 6, once the pusher end 142 is within the housing 100, it then engages the device 130 upon further distal advancement. The pusher 140 then pushes the device 130 distally to break through the breakaway distal end 102 of the housing 100.

Further advancement of the pusher 140 causes the device 130 to be released from the housing. Once released, the device 130 is permitted to expand for deployment. Such a device is shown and described in the aforementioned U.S. Pat. No. 6,258,100. As previously mentioned, other forms of bronchial obstruction devices may be deployed with the present invention. Such devices may be one-way valves, totally blocking, expandable, or non-expandable.

Figure 8:
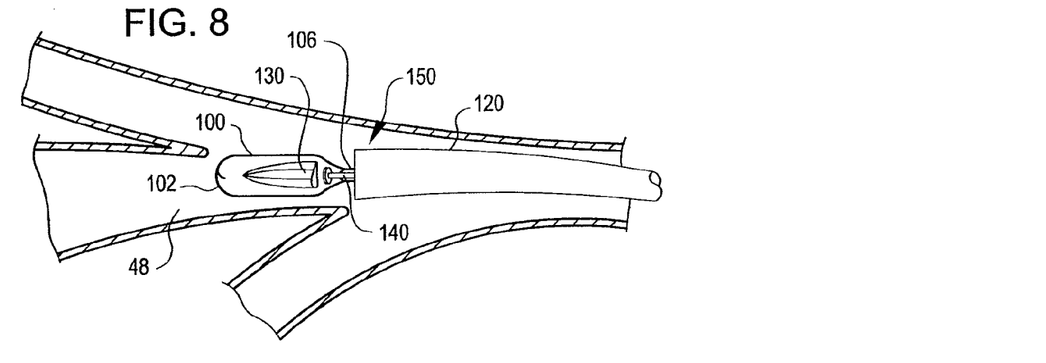
FIG. 8 is a side view illustrating an intermediate step in deploying a bronchial obstruction device in accordance with an embodiment of the present invention.
Figure 9:
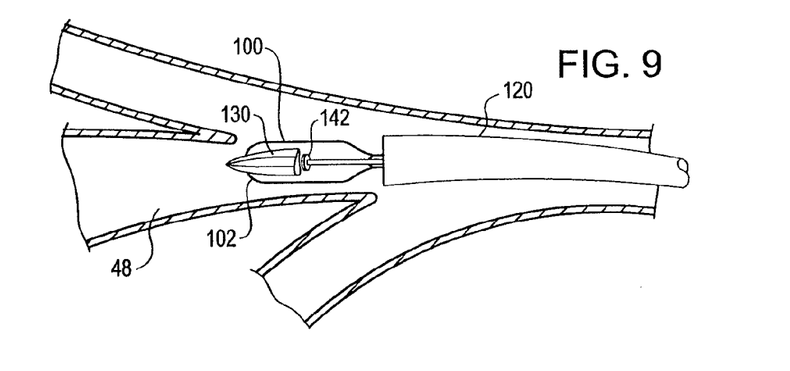
FIG. 9 is another side view illustrating a further step in the deployment of the device.
Figure 10:
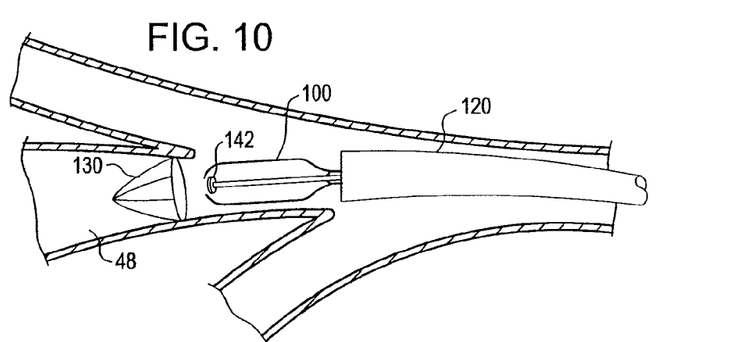
FIG. 10 is a side view illustrating the device after deployment.

FIGS. 8-10 show a complete system 150 embodying the present invention deploying the device 130 within an air passageway, such as bronchial branch sub-branch 48. The system 150 generally includes the conduit 120, the housing 100, the housing extension 106, and the pusher 140 as previously described. In FIG. 8 it may be seen that the conduit 120 has been advanced such that its distal end is just proximal to the bronchial sub-branch 48. The housing 100 has also been advanced through the conduit so that its distal end 102 is within the bronchial sub-branch 48. The pusher has also been advanced into the housing 100 for engagement with the device 130.

As seen in FIG. 9, the pusher end 142 is within the housing 100. It then engages the device 130 and upon further distal advancement, the pusher 140 pushes the device 130 distally to break through the breakaway distal end 102 of the housing 100.

Further advancement of the pusher 140 causes the device 130 to be released from the housing in the bronchial sub-branch 48. Once released, the device 130 is permitted to expand for deployment in the bronchial sub-branch 48. Again, the device 130 may be of the type shown and described in the aforementioned U.S. Pat. No. 6,258,100. The now expanded device 130 serves to obstruct the bronchial sub-branch 48 for collapsing the lung portion communicating with the bronchial sub-branch 48.

Although the invention(s) presented herein have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the invention(s) herein disclosed should not be limited by the particular embodiments described above, but should be determined only by a fair reading of the claims that follow.

What is claimed is:

1. An apparatus for deploying a bronchial device in an air passageway, the apparatus comprising:
   a conduit configured to be passed down a trachea, the conduit comprising an internal lumen,
   an axially-movable push rod within the internal lumen,
   a housing that defines a sealed capsule that is movable relative to the conduit, the sealed capsule substantially sealingly enclosing and separating the bronchial device from an environment external to the capsule, the bronchial device positioned within the housing, and
   the housing being further arranged to be advanced down the internal lumen of the conduit placed into the air passageway in the direction of a distal end of the housing and, upon movement of the axially-movable push rod from outside of the capsule into a proximal end of the sealed capsule and upon application of force by the axially-movable push rod on a proximal end of the bronchial device, the bronchial device is released through a distal end of the capsule for deployment in the air passageway such that the bronchial device is not in physical contact with the housing or the conduit once deployed.

2. The apparatus of claim 1, wherein the housing further comprises an openable feature through which the bronchial device is released.

3. The apparatus of claim 2, wherein the openable feature is opened by being broken.

4. The apparatus of claim 1, wherein the housing comprises a break-away portion through which the axially-movable push rod extends to contact the bronchial device.

5. The apparatus of claim 1, wherein the sealed capsule comprises an openable feature at one end and a break-away feature at a second end.

6. The apparatus of claim 5, wherein the push rod can break through the break-away feature to urge the bronchial device through the openable feature.

7. The apparatus of claim 1, wherein the push rod extends within a lumen defined within a tubular extension attached to the housing.

8. The apparatus of claim 7, wherein the tubular extension is configured to deform as the axially-movable push rod is advanced through the tubular extension.

9. The apparatus of claim 1, wherein the housing includes a flexible material for collapsing within an internal lumen of the conduit.

10. The apparatus of claim 1, wherein the axially-movable push rod is located outside of the capsule until the application of force onto the proximal end of the capsule.

11. The apparatus of claim 1, wherein the capsule is configured to be fully within the conduit.

12. The apparatus of claim 1, wherein the capsule is configured to be broken on both the proximal and distal ends.

13. The apparatus of claim 12, wherein upon movement of the axially-movable push rod from outside of the capsule, the axially-movable push rod breaks the proximal end of the capsule, contacts the bronchial device at a proximal end, and pushes against the proximal end of the bronchial device so that a distal end of the bronchial device breaks the distal end of the capsule.

14. The apparatus of claim 1, wherein the sealed capsule is located distal of the distal end of the axially-movable push rod prior to movement of the axially-movable push rod from outside of the sealed capsule into a proximal end of the sealed capsule.

15. A system for deploying a bronchial device in an air passageway, the system comprising:
   a catheter configured to be passed down a trachea, into a bronchus communicating with the trachea and into the air passageway communicating with the lung portion, the catheter comprising an internal lumen;
   an axially-movable pusher within the internal lumen;
   a housing that defines a sealed capsule arranged to substantially sealingly encapsulate and separate the bronchial device from an environment external to the capsule, the housing configured to be fully within the catheter; the pusher movable relative to the housing the bronchial device positioned within the sealed capsule, the housing being further arranged to be advanced down an internal lumen of the catheter placed into the air passageway in the direction of a distal end of the catheter, and to release the bronchial device, upon movement of the axially-movable pusher from outside of the capsule into a proximal end of the sealed capsule and upon application of a force on a proximal end of the bronchial device, for deployment through a distal end of the sealed capsule in the air passageway such that the bronchial device is not in physical contact with the housing or the catheter once deployed, the axially-movable pusher being located outside of the sealed capsule until the application of the force on the proximal end of the sealed capsule; and
   the housing comprising a proximally extending tubular extension that is separated from the bronchial device by a wall defining the sealed capsule.

16. The system of claim 15, wherein the housing further comprises an openable end through which the bronchial device is released.

17. The system of claim 16, wherein the wall is breakable to place an inside of the capsule into communication with a lumen defined by the tubular extension.

18. The system of claim 15, wherein the housing comprises a break-away portion arranged upon breakage to release the bronchial device.

19. The apparatus of claim 15, wherein upon movement of the axially-movable pusher from outside of the capsule, the axially-movable pusher breaks the proximal end of the capsule, contacts the bronchial device at a proximal end, and pushes against the proximal end of the bronchial device so that a distal end of the bronchial device breaks the distal end of the housing.

* * * * *